United States Patent [19]

Andrews et al.

[11] 3,994,936

[45] Nov. 30, 1976

[54] CATALYTIC REARRANGEMENT

[75] Inventors: David Arthur Andrews, Upper Montclair, N.J.; Nathan Chadwick Hindley, Welwyn Garden City, England

[73] Assignee: Hoffmann-La Roche Inc., Nutley, N.J.

[22] Filed: Mar. 27, 1975

[21] Appl. No.: 562,750

Related U.S. Application Data

[63] Continuation of Ser. No. 410,930, Oct. 24, 1973, Pat. No. 3,912,656.

[52] U.S. Cl. .................. 260/397.4; 260/586 R; 260/592; 260/593 R; 260/598; 260/601 R; 252/430

[51] Int. Cl.² ............... C07J 5/00; C07C 45/00

[58] Field of Search ............ 260/397.4, 586 R, 592, 260/593 R, 598, 601 R; 252/430

[56] References Cited

UNITED STATES PATENTS 3,920,751   11/1975   Chabardes et al. .................. 260/601

*Primary Examiner*—Elbert L. Roberts
*Attorney, Agent, or Firm*—Samuel L. Welt; Bernard S. Leon; William H. Epstein

[57] ABSTRACT

Process for converting secondary and tertiary acetylenic carbinols to the corresponding alpha,beta-unsaturated carbonyl compounds by rearranging the carbinol with (trilower alkyl-, tricycloalkyl-, triaryl- or triarylalkyl-siloxy)-vanadium oxide catalyst in the presence of a silanol where either the vanadium oxide or the silanol contains a phenyl group substituted with at least one electron withdrawing group.

26 Claims, No Drawings

3,994,936

CATALYTIC REARRANGEMENT

CROSS REFERENCE TO RELATED APPLICATIONS

This application is a continuation in part application of Ser. No. 410,930 filed Oct. 24, 1973, Andrews and Hindley, now U.S. Pat. No. 3,912,656. Also related to this application is U.S. patent application Ser. No. 248,046, filed Apr. 27, 1972, Pauling.

BACKGROUND OF THE INVENTION

Certain alpha,beta-mono-unsaturated aldehydes have heretofore been obtained by the catalytic rearrangement of corresponding tertiary acetylenic carbinols or derivatives thereof. For example, acetylenic carbinols have been converted to unsaturated aldehydes by a process involving initially esterifying the carbinols and then rearranging the ester derivative with the aid of a silver or copper catalyst. Typically, such rearrangement reactions have required several process steps, including the formation of an allene ester intermediate.

In an effort to reduce the number of process steps required for such catalytic rearrangement processes, catalysts derived from a metal of the Vth to VIIth subgroup of the periodic chart, particularly vanadium, niobium, molybdenum, tungsten and rhenium, have been utilized instead of copper or silver catalysts. See British Pat. No. 1,204,754. Such catalysts have permitted acetylenic carbinols to be expeditiously rearranged to unsaturated aldehydes in a single operation. However, the use of such catalysts to the Vth to VIIth subgroup has not been found to be completely satisfactory. Considerable loss of catalyst activity has been found to inevitably occur during the course of the rearrangement reaction. In addition, it has been discovered that decomposition products are formed during the rearrangement reaction as the catalyst loses activity and that these decomposition products cause the aldehyde product to be destroyed as it is formed, thereby reducing product yields.

The catalysts used hitherto for such isomerization reactions have the disadvantage that they are relatively unstable and can only be used once or a few times. In contradistinction thereto the present catalyst system is more stable and useful for a great number of isomerizations. Moreover, the isomerization in the presence of the present catalyst system can be carried out in an advantageous time interval at temperatures between room temperature and about 150° C. This is especially significant in the case of thermolabile starting materials and end products.

SUMMARY OF THE INVENTION

In accordance with this invention, it has been discovered that tertiary or secondary acetylenic carbinols can be converted with the corresponding alpha, beta-unsaturated aldehydes or ketones utilizing a hydrocarbon siloxy-vanadium oxide catalyst with the addition of a hydrocarbon silanol wherein at least either the catalyst or the silanol contain at least one phenyl substituent activated through substitution by one or more electron-withdrawing groups. By using the above combination of the silanol and the siloxy vanadium oxide catalyst, the secondary or tertiary acetylenic carbinol is converted into the alpha,beta-unsaturated aldehyde or ketone in very high yields and with high conversions.

It has been found that the use of the aforementioned silanol in the conversion of a secondary or tertiary acetylenic carbinol to the corresponding alpha,beta unsaturated carbonyl compound reduces any loss of the activity of the vanadium oxide catalyst. Therefore, this catalyst can be reused for many subsequent reaction batches without any loss of yield of the aldehyde or ketone produced by this process. Furthermore, the use of the aforementioned silanol in the reaction medium minimizes the production of decomposition products which would reduce the yields of the carbonyl compound. Therefore, the presence of the aforementioned silanol in the reaction medium permits the catalyst to be reused over and over again without any deactivation or loss of yield.

Furthermore, a catalyst system is provided in accordance with this invention containing the aforementioned vanadium oxide catalyst and the aforementioned silanol. This system, which is utilized for the rearrangement of the tertiary or secondary acetylenic carbinols can be reused, after removal of the rearrangement product, by simply adding another batch of the tertiary or secondary acetylenic carbinol to this system.

By use of this catalyst and silanol where either one or both these materials contain at least one phenyl substituent substituted with at least one electron withdrawing group, the isomerization of this invention can, if desired, be carried out at low temperatures, i.e., from about room temperature to about 150° C. without the need for utilizing extreme elevated temperatures. This is extremely advantageous in the case where either the starting materials and end products are thermolabile.

The advantage obtained by utilizing the aforementioned catalysts and silanol can be seen in the case of 3,7-dihydroxy-3,7-dimethyl-oct-1-yne and 2,5-dihydroxy-2,5-dimethyl-hex-3-yne, which largely decomposes at above 120° C. and which cannot be isomerized with known catalysts which work predominantly in the range of this temperature. In accordance with this invention, these compounds can now be isomerized to 7-hydroxy-3,7-dimethyl-oct-2-en-1-al and 2-hydroxy-2,5-dimethyl-hex-4-en-3-one respectively in good yields using the novel catalysts system of this invention at a temperature between room temperature (i.e. about 20° C.) and about 100° C.

DETAILED DESCRIPTION

In accordance with this invention, any secondary and tertiary acetylenic carbinol can be rearranged to the corresponding alpha, beta-unsaturated carbonyl compound utilizing a (trilower alkyl-, tricycloalkyl, triaryl or triarylalkyl-siloxy)-vanadium oxide catalyst in the presence of a silanol where either or both the vanadium oxide catalyst or the silanol contains a phenyl substituent which is substituted with at least one electron withdrawing group.

The secondary or tertiary acetylenic carbinols are those carbinols, where the acetylene linkage is between the alpha and beta carbon atoms from the carbon atom bearing the hydroxy substituent. Among the preferred secondary and tertiary carbinols are compounds of the formula:

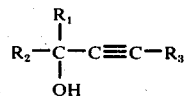

wherein $R_1$ is hydrogen or lower alkyl, $R_2$ is alkyl, alkenyl, cycloalkyl-substituted-alkenyl, cycloalkyl substituted alkyl, phenyl-alkyl, phenyl-alkenyl, phenyl, cycloalkyl, cycloalkenyl, cycloalkenyl-substituted alkyl, and cycloalkenyl substituted alkenyl; $R_1$ and $R_2$ taken together with their attached carbon atom form a cycloalkyl or cycloalkenyl group, or cycloalkyl or cycloalkenyl condensed with one or more saturated or unsaturated cycloalkyl groups; $R_3$ is hydrogen, alkyl, alkenyl, phenyl alkyl, phenyl alkenyl, cycloalkyl-substituted alkenyl, cycloalkyl substituted-alkyl, cycloalkenyl-substituted alkyl, cycloalkenyl substituted alkenyl, phenyl, cycloalkyl or cycloalkenyl and wherein said alkyl, alkenyl, cycloalkyl, cycloalkenyl and phenyl groups are unsubstituted or substituted in one or more positions with lower alkyl, lower alkoxy, hydroxy, lower alkanoyl, aroyl, lower alkanoyloxy or aroyloxy; and wherein said alkyl, alkenyl, cycloalkyl and cycloalkenyl groups can also be substituted in one or more positions with an additional substituent selected from the group consisting of oxo or ketalized-oxo.

The preferred secondary or tertiary carbinols of formula I are isomerized, in accordance with this invention to compounds of the formula:

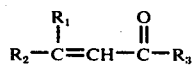

wherein $R_1$ $R_2$ and $R_3$ are as above.

The compounds of formula I are rearranged to the compounds of formula II in accordance with this invention, in the presence of a catalyst of the formula:

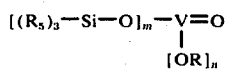

wherein $R_5$ is a hydrocarbon selected from the group consisting of lower alkyl, cycloalkyl, phenyl, phenyl (lower alkyl), phenyl substituted in one or more positions with an electron withdrawing group and phenyl-lower alkyl wherein the phenyl substitutent is substituted in one or more positions with an electron withdrawing group; R is $R_5$ or $-Si-(R_5)_3$; m is an integer of from 1 to 3; and n is an integer of from 0 to 1 with the proviso that the sum of m and n is 3;
and a silanol of the formula:

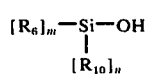

wherein $m$ and $n$ are as above; $R_6$ and $R_{10}$ are lower alkyl, cycloalkyl, phenyl, phenyl-lower alkyl, phenyl substituted in one or more positions with an electron withdrawing group or phenyl-lower alkyl where the phenyl substitutent is substituted in one or more positions with an electron withdrawing group;
with the proviso that one of $R_5$, $R_6$ or $R10$ is a phenyl or phenyl-lower alkyl group with the phenyl moity substituted in one or more positions with an electron withdrawing group.

Among the preferred catalysts of the formula III above are the following:

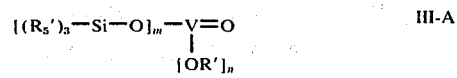

wherein $m$ and $n$ are as above; $R_5'$ is a hydrocarbon group selected from lower alkyl, cycloalkyl, phenyl, phenyl(lower alkyl) and $R'$ is $R_5'$ or a $-Si(R_5')_3$;
and

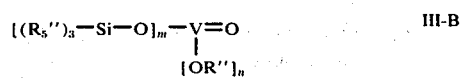

wherein $m$ and $n$ are as above; $R_5''$ is phenyl substituted in one or more positions by an electron-withdrawing group and $R''$ is $R_5'$ or $R_5''$.

Of the silanols of the formula IV above, the following are preferred:

wherein m, n, $R_5''$ and $R''$ are as above;
and

wherein $m$, $n$ and $R_5'$ are as above.

The lower alkyl groups denoted by $R_1$ include both straight-chain and branched-chain hydrocarbon groups containing 1–6 carbon atoms such as methyl, ethyl, propyl, isopropyl and the like.

The alkyl groups which are denoted by $R_2$ and $R_3$ and which may be substituted can contain from 1 to 30 carbon atoms preferably from 1 to 20 carbon atoms and can be straight-chain or branched-chain.

The alkenyl groups denoted by $R_2$ and $R_3$ designated alkenyl groups containing from 2 to 30, preferably from 2 to 20 carbon atoms. The cycloalkenyl groups preferably containing from 3 to 7 carbon atoms such as cyclopropenyl, cyclopentenyl, cyclohexenyl, etc.

Among the preferred catalyst or silanols of formula III and IV are those where the phenyl group contains from 1 to 4, preferably from 1 to 3 electron withdrawing substituents.

As examples of cycloalkyl and cycloalkenyl groups are those which contain from 3 to 7, preferably 3 to 6 carbon atoms. Among the preferred unsubstituted or alkyl substituted cycloalkenyl or cycloalkyl groups denoted by $R_2$ there may be mentioned the following:
cyclohex-1-yl,
2,6,6-trimethyl-cyclohex-1-yl,
3-methyl-cyclohex-3-en-1-yl and
4-methyl-cyclohex-3-en-1-yl.

The alkyl substituted cycloalkenyl or cycloalkyl groups depicted by $R_2$ can contain from 4 to 20 carbon atoms. As examples of alkenyl or alkyl groups denoted by $R_2$ there may be mentioned the following: of the lower members preferably the methyl, hexyl and ethyl groups and of the higher members those which preferably have an isoprene or isoprene-like structure such as:

4-methyl-pent-3-enyl;
3,4-dimethyl-pent-3-enyl;
4,8-dimethyl-nona-3,7-dienyl;
1-ethyl-4-methyl-pent-3-enyl;
4,8,12-trimethyl-tridecyl;
4,8,12-trimethyl-trideca-3,7,11-trienyl;
4-hydroxy-4-methyl-pentyl; and
4-methoxy-4-methyl-pentyl groups. Examples of unsubstituted or substituted alkyl or alkenyl groups denoted by $R_3$ are: of the lower members the propyl group and 2-hydroxy-prop-2-yl group and of the higher members the 2,6-dimethyl-hept-1,3,5-trienyl group.

The aforementioned optionally substituted cycloalkyl or cycloalkenyl alkyl or alkenyl component designated by $R_2$ can contain from 3 to 20 carbon atoms. Examples of such cycloalkyl groups linked with a straight-chain or branched-chain alkyl or alkenyl group $R_2$, preferably one having an isoprene or isoprenelike structure, are the following:

2-(2,6,6-trimethyl-cyclohex-1-en-1-yl)-vinyl;
2-(4-oxo-2,6,6-trimethyl-cyclohex-1-en-1-yl)-vinyl;
2-(4,4-ethylenedioxy-2,6,6-trimethyl-cyclohex-1-en-1-yl)-vinyl
6-(2,6,6-trimethyl-cyclohex-1-en-1-yl)-4-methyl-hexa-1,3,4-trienyl;
6-(4-oxo-2,6,6-trimethyl-cyclohex-1-en-1-yl)-4-methyl-hexa1,3,5-trienyl; and
6-(4,4-ethylenedioxy-2,6,6-trimethyl-cyclohex-1-en-1-yl)-4-methyl-hexa-1,3,5-trienyl groups.

Examples of carbinol starting materials of formula I in which $R_1$ and $R_2$ are joined together to form a substituted or unsubstituted cycloalkyl or cycloalkenyl which can contain from 3 to 20 carbon atoms are:

1-ethynyl-cyclopentanol;
1-ethynyl-cyclohexanol;
1-ethynyl-2,6,6-trimethyl-cyclohexanol;
4-ethynyl-4-hydroxy-1-oxo-3,5,5-trimethyl-cyclohex-2-ene; and
4-ethynyl-4-hydroxy-1,1-ethylenedioxy-3,5,5-trimethyl-cyclohex2-ene.

Examples of carbinol starting materials of formula I in which $R_1$ and $R_2$ are joined together to form a cycloalkyl group which is condensed with one or more saturated or unsaturated cycloalkyl groups are:

Pregn-5-en-20-yn-3beta,17-diol;
17-hydroxy-19-nor-pregn-5(10)-en-20-yn-3-one;
13-ethyl-17-hydroxy-18,19-di-nor-17alpha-pregn-4-en-20-yn3-one[norgestrel]; and
3-methoxy-19-nor-pregn-1,3,5(10)-trien-20-yn-17-ol [mestranol].

When $R_2$ and $R_3$ are joined together to form a ring or system in the aforementioned manner, this can contain from 5 to 30 carbon atoms.

The substituents which may be present on the aforementioned alkyl, alkenyl, cycloalkyl, cycloalkenyl and phenyl groups are lower alkyl groups containing from 1–6 carbon atoms (e.g. methyl, ethyl, propyl, isopropyl and the like), lower alkoxy groups containing 1–6 carbon atoms (e.g. methoxy, ethoxy, propoxy, isopropoxy and the like), lower alkanoyl groups containing 1–6 carbon atoms (e.g. formyl, acetyl, propionyl, butyryl and the like), aroyl groups (especially the benzoyl group), lower alkanoyloxy groups containing 1–6 carbon atoms (e.g. acetoxy, propionyloxy, butyryloxy and the like) and aroyloxy groups (especially the benzoyloxy group). The alkyl, alkenyl, cycloalkyl and the cycloalkenyl groups may also be substituted by oxo or by ketalized-oxo. An oxo group can be ketalized with a lower alkanol (e.g. methanol) or glycol (e.g. ethyleneglycol). The group denoted by $R_5$ in formula III and $R_6$ in formula IV is preferably a lower alkyl group containing from 1 to 7 carbon atoms (e.g. methyl, ethyl, isopropyl or n-butyl), a higher alkyl group containing from 8 to 20 carbon atoms (e.g. octyl, decyl, dodecyl, pentadecyl, octadecyl) or a phenyl group, a lower alkyl-substituted phenyl group (e.g. tolyl or xylyl) or a phenyl-(lower alkyl) group (e.g. benzyl or phenethyl) or a cyclohexyl group.

Of the oxo compounds of formula II hereinbefore, the following five groups represented by formulae IIA, IIB, IIC, IID and IIE are especially important:

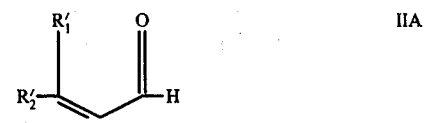

IIA wherein $R'_1$ and $R'_2$ taken together form a cycloalkyl or cycloalkenyl which may be unsubstituted or substituted with lower alkyl, lower alkoxy, hydroxy, oxo or ketalized oxo;

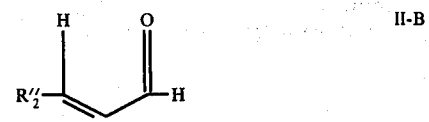

II-B wherein $R''_2$ is cycloalkyl, cycloalkenyl or phenyl which may be unsubstituted or substituted by lower alkyl, lower alkoxy, hydroxy or except in the case of phenyl, by oxo or ketalized oxo:

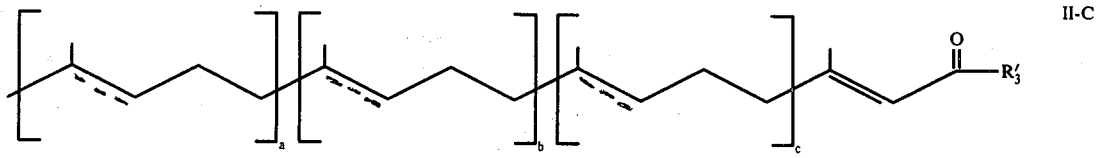

II-C wherein $R'_3$ is hydrogen atom or lower alkyl and $a=1$, $b=1$ and $c=1$ or $a=0$, $b=1$ and $c=1$ or $a=0$, $b=0$ and $c=1$ or $a=0$, $b=0$ and $c=0$ and the broken lines can be hydrogenated or denote contain carbon to carbon bonds; and wherein hydroxy, lower alkoxy or both hydroxy and lower alkoxy substituents may be substituted on the carbon atoms in the groupings $a$, $b$ and/or $c$;

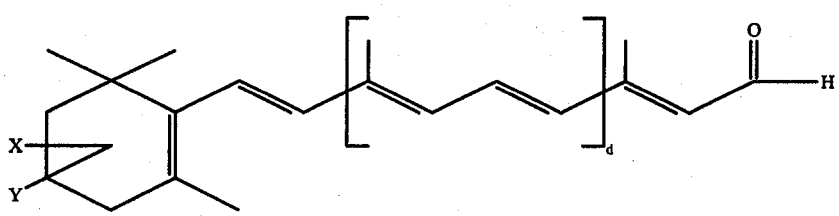
II-D wherein $d=0$ or 1; X is hydrogen or hydroxy and Y is oxo or hydrogen; and

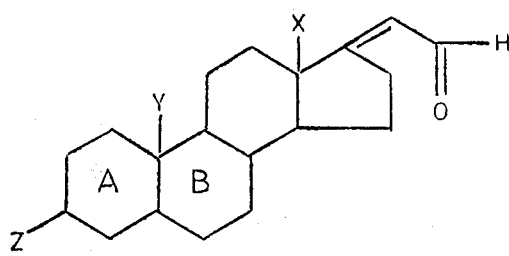

II-E wherein X is lower alkyl, Y is hydrogen or lower alkyl, Z is hydroxy, oxo, alkoxy or acyloxy group

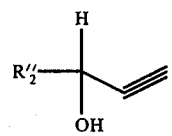

I-B wherein $R''_2$ is as above.

Examples of the compound of formula I-D are 3-hydroxy-3-phenyl-prop-1-yne.

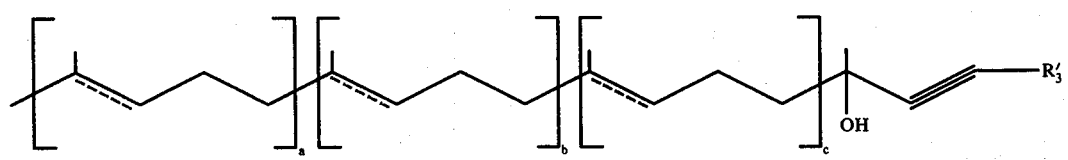

I-C and wherein the A-ring can be wholly or partially unsaturated and the B-ring can be partially unsaturated.

The carbinols of formula I required as starting materials for the manufacture of the oxo compounds of formula II-A, II-B, II-C, II-D and II-E hereinbefore have the following general formulae:

wherein $R'_3$, $a$, $b$ and $c$ and the broken lines are as above;

and wherein hydroxy and/or lower alkoxy substituents may be present on the groupings $a$, $b$ and/or $c$.

Examples of compounds of the formula I-C are:
3-methyl-but-1-yn-3-ol;
2-hydroxy-2-methyl-hept-3yne;
3-hydroxy-3,7-dimethyl-oct-6-en-1-yne;
3,7-dihydroxy-3,7-dimethyl-oct-1-yne;
3-hydroxy-3-methoxy-3,7-dimethyl-oct-1-yne; 3-hydroxy-3,7,11-trimethyl-dodeca-6,10-dien-1-yne; and
3-hydroxy-3,7,11,15-tetramethyl-hexadec-1-yne.

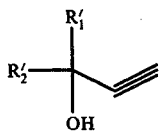

I-A wherein $R'_1$ and $R'_2$ are as above.
Examples of compounds of the formula I-A are:
1-ethynyl-cyclohexanol;
1-ethynyl-2,6,6-trimethyl-cyclohexanol; and
4-ethynyl-4-hydroxy-1,1-ethylenedioxy-3,5,5-trimethyl-cyclohex-2-ene.

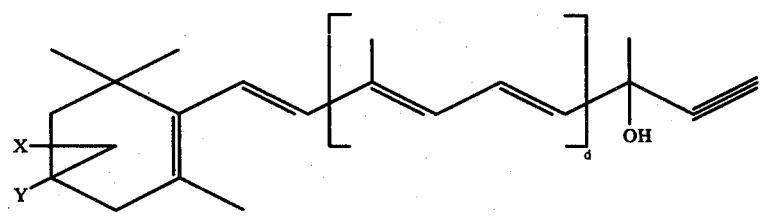

I-D wherein $d$ and X and Y are as above.
Examples of the compound of formula I-D are:
5-(2,6,6-trimethyl-cyclohex-1-en-1-yl)-3-hydroxy-3-methylpent-4-en-1-yne;
9-(2,6,6-trimethyl-cyclohex-1-en-1-yl)-3-hydroxy-3,7-dimethyl-nona-4,6,8-trien-1-yne;

9-(4-oxo-2,6,6-trimethyl-cyclohex-1-en-1-yl)-3-hydroxy3,7-dimethyl-nona-4,6,8-trien-1-yne; and 9-(4,4-ethylenedioxy-2,6,6-trimethyl-cyclohex-1-en-1-yl)-3-hydroxy-3,7-dimethyl-nona-4,6,8-trien-1-yne.

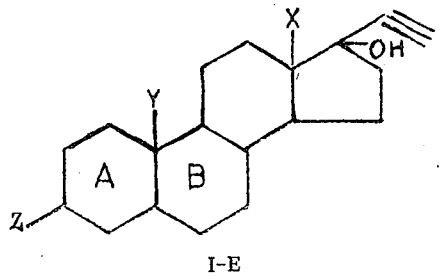

I-E wherein X, Y and Z are as above and the A-ring can be wholly or partially unsaturated and the B-ring can be partially unsaturated.

Examples of compounds of the formula I-E are:
pregn-5-en-20-yn-3beta,17-diol;
17-hydroxy-19-nor-pregn-5(10)-en-20-yn-3-one;
13-ethyl-17-hydroxy-18,19-di-nor-17alpha-pregn-4-en-20-yn3-one [norgestrel]; and
3-methoxy-19-nor-pregn-1,3,5(10)-trien-20-yn-17-ol [mestranol].

The process of the present invention has proved to be particularly favorable and advantageous for the manufacture of the following oxo compounds of formula II:
Senecioaldehyde [prenal];
3-methyl-pent-2-en-1-al;
3,7-dimethyl-4-ethyl-octa-2,6-dien-1-al;
non-2-en-1-al;
citral; [3,7-dimethyl-octa-2,6-dien-1-al] 7-(hydroxy or methoxy)-citral; [7(hydroxy or methoxy)-3,7-dimethyl-oct-2-en-1-al]
farnesal;
phytal;
cyclohexylidene-acetaldehyde;
2,6,6-trimethyl-cyclohexylidene-acetaldehyde; cinnamaldehyde [3-phenylpropenal] $\beta$-$C_{15}$-aldehyde [5-(2,6,6-trimethyl-cyclohex-1-en-1-en-1-yl)-3-methyl-penta-2,4-dien-1-al]
vitamin A aldehyde;
2-methyl-hept-2-en-4-one; 2,5-dimethyl-hex-2-en-5-ol-4-one; 17-(formylmethylene)-androst-5-en-3 $\beta$-ol; 17-(formylmethylene)-estr-5(10)-en-3-one; 13 $\beta$-ethyl-17-(formylmethylene)-gon-4-en-3-one; and
3-methoxy-19-nor-pregn-1,3,5(10),17(20)-tetraen-21-al.

Of the catalysts of the formula III-A employed in accordance with the present invention, those of the general formula:

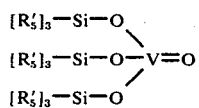

III-AA wherein $R_5'$ is as above;
occupy a preferred position. In an especially preferred aspect, $R_5'$ is an alkyl, cycloalkyl, phenyl or phenyl-(lower alkyl) group. Particular examples of catalysts of the formula III-AA are:
tris-[trimethyl-siloxy]-vanadium oxide,
tris-[tricyclohexyl-siloxy]-vanadium oxide and
tris-[triphenyl-siloxy]-vanadium oxide.

The catalysts of the formula III-A and III-AA are known compounds. They can be prepared according to methods known per se; for example, by i. the reaction of, for example, vanadium pentoxide with, for example, a trialkyl silanol of the formula [alkyl]$_3$SiOH or a triphenyl silanol of the formula [phenyl]$_3$SiOH with azeotropic removal of the water formed in the reaction with the aid of an entraining agent such as, for example, benzene.

ii. the reaction of, for example, vanadium oxytrichloride with, for example, a trialkyl silanol or triphenyl silanol in the presence of a base such a pyridine or ammonia;

iii. the reaction of, for example, vanadium oxytrichloride with, for example, a trialkyl alkali silanolate of the formula [alkyl]$_3$SiOMe(I) or a triphenyl alkali silanolate of the formula [phenyl]$_3$SiOMe(I), wherein Me indicates an alkali metal;

iv. the reaction of, for example, a vanadium acid ester of the formula [alkoxy]$_3$-V=O with, for example, a trialkyl silanol or triphenyl silanol in the presence of catalytic amounts of an alkyl- or phenyl-alkali silanolate (e.g. a trialkyl alkali silonolate;

v. the reaction of, for example, a siloxy-vanadium oxide of the formula [(alkyl)$_3$-Si-O]$_3$-V=O with a trialkyl silanol or triphenyl silanol, if necessary in the presence of catalytic amounts of an alkali silanoate such as a tri-(lower alkyl)-alkali silanolate.

vi. the reaction of, for example, silver orthovanadate of the formula Ag$_3$VO$_4$ with, for example, a trialkyl silyl halide of the formula [alkyl]$_3$SiCl or a triphenyl silyl halide of the formula [phenyl]$_3$SiCl in a solvent such as, for example, benzene or methylene chloride;

vii. the reaction of, for example, vanadium pentoxide with, for example, a hexaalkyl disiloxane of the formula [alkyl]$_3$SIoSi[alkyl]$_3$ at an elevated temperature, for example at about 100° C, or viii. the double reaction of a vanadium acid ester of the formula [alkoxy]$_3$-V=O with a trialkyl silyl ester or triphenyl silyl ester, for example, of tripropyl orthovanadate with trimethyl silyl acetate with the expulsion of propyl acetate.

Of the catalysts of the formula III-B employed in accordance with the present invention, those of the general formula:

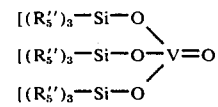

III-BB wherein $R_5''$ is as above;
occupy a preferred position.

The phenyl group denoted by $R_5''$ in the catalysts of the formula III-B and III—BB must carry one or more, preferably from 1 to 3, electron-withdrawing substituted whereas the phenyl group denoted by $R_5$ in the catalysts of formula III can be unsubstituted or carry one or more, preferably from 1 to 3, of such electron withdrawing substituents. Any conventional electron withdrawing substituent may be present on the phenyl ring moiety.

Included among the electron-withdrawing substituents are particularly those substituents listed in "Textbook of Organic Chemistry", Fieser and Fieser, 1954

Ed., page 651, namely —NO₂, —CN, —COCH₃, —CHO, —COOC₂H₅, —Cl, —Br, —I and —COOH, as well as —F, —CF₃ and —C₆H₅.

Examples of catalysts of the formulae III, III-B and III-BB hereinbefore are:
 tris-[tri-(p-fluorophenyl)-siloxy]-vanadium oxide,
 tris-[tri-(p-chlorophenyl)-siloxy]-vanadium oxide,
 tris-[tri-(p-bromophenyl)-siloxy]-vanadium oxide,
 tris-[tri-(α,α,α-trifluoro-m-tolyl)-siloxy]-vanadium oxide,
 tris-[tri-(α,α,α-trifluoro-p-tolyl)-siloxy]-vanadium oxide,
 tris-[bis-(3-nitro-4-bromophenyl)-(4-bromophenyl)-siloxy]-vanadium oxide,
 (tri-p-fluorophenyl)-siloxy-bis(triphenyl-siloxy)-vanadium oxide,
 tris-[3,5-dinitrophenyl siloxy]-vanadium oxide,
 tris-(3-nitrophenyl siloxy]-vanadium oxide,
 tris-[tri-(4-biphenylyl)-siloxy]-vanadium oxide,
 bis-[tri-(p-fluorophenyl)-siloxy]-triphenyl-siloxy-vanadium oxide, and
 bis-[tri-(p-bromophenyl)-siloxy]-cyclohexyloxy-vanadium oxide.

The catalysts of the formulae III, III-B and III-BB can be prepared according to methods known per se; for example, by i. the reaction of vanadium pentoxide with a silanol of the formula (R₅″)₃SiOH wherein R₅″ is as above with azeotropic removal of the water formed in the reaction with the aid of an entraining agent such as, for example, benzene;

ii. the reaction of vanadium oxytrichloride with a silanol of the formula (R₅″)₃SiOH wherein R₅″ is as above in the presence of a base such as, for example, pyridine or ammonia;

iii. the reaction of vanadium oxytrichloride with an alkali silanolate of the formula (R₅″)₃SiOMe(I) wherein Me is an alkali metal in an inert solvent such as diethyl ether;

iv. the reaction of a vanadium acid ester of the formula [alkoxy]₃-V=O with a silanol of the formula (R₅′λ′)₃SiOH if necessary in the presence of catalytic amounts of an alkyl- or phenyl-alkali silanolate (e.g. a trialkyl alkali silanolate);

v. the reaction of a siloxy-vanadium oxide of the formula [(alkyl)₃SiO]₃-V=O with a silanol of the formula (R₅″)₃SiOH, if necessary in the presence of catalytic amounts of an alkali silanoate such as a tri-(lower alkyl)-alkali silanoate.

vi. the reaction of silver orthovanadate of the formula Ag₃VO₄ with a sily halide of the formula (R₅″)₃-Si-Hal in a solvent such as, for example, benzene or methylene chloride; or vii. the double reaction of a vanadium acid ester of the formula [alkoxy]₃-V=O with a silyl ester of the formula (R₅″)₃-Si-O-COOalk such as with tripropyl orthovanadate with the expulsion of propyl acetate, conveniently in a solvent such as n-heptane in which the resulting ester forms an azeotrope which can be separated from the reaction mixture.

Of the silanols of the formula IV-B employed in accordance with the present invention are those of the formula:

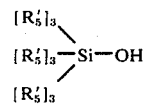

wherein R₅′ is as above;
occupy a preferred position.

Examples of silanols of the formula IV-BB are:
 triphenyl-silanol and tricyclohexyl-silanol.

Of the silanols of the formula IV-A employed in accordance with the present invention are those of the formula:

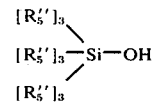

wherein R₅″ is as above;
occupy a preferred position.

Examples of silanols of the formula IV-AA are:
 tri-(p-fluorophenyl)-silanol,
 tri-)p-chlorophenyl)-silanol,
 tri-(p-bromophenyl)-silanol,
 tri-(4-biphenylyl)-silanol, and
 tris-(α,α,α-trifluoro-p-tolyl)-silanol.

The catalyst system used in the isomerization reaction can be prepared by mixing the silanol of formula IV and the vanadata catalyst of formula III. This mixture which is utilized to isomerize the compound of formula II contains at least 0.05 mole percent of the silanol of formula IV based upon the moles of the vanadate catalyst of formula III in the mixture. The mixture utilized to isomerize the compound of formula I can contain a large excess of silanol, i.e., 85,000 mole percent or greater of the silanol of formula IV, based upon the mole percent of the vanadate catalyst of formula III. Generally, it is preferred that the mixture contain from about 5 mole percent to 65,000 mole percent of the silanol of formula IV, based upon the moles of the vanadate catalyst contained in the mixture. Mixtures containing from 25 mole percent to 8,500 mole percent of the silanol of formula IV based on the moles of the vanadate of formula III are especially preferred. The compound of formula I can be added to the mixture or the mixture can be added to the compound of formula I in order to carry out the isomerization reaction.

The catalytic isomerization of acetylenic carbinols of formula I to alpha,beta-unsaturated oxo compounds of formula II in accordance with the present invention is expediently carried out by reacting the corresponding carbinol together with the catalyst system containing the vanadate catalyst of formula III and silanol of formula IV. The catalytic isomerization is expediently carried out using about 0.1 to about 20 mole percent, preferably about 1.5 to about 2 mole percent of catalyst of formula III based on the moles of the compound of formula II.

The silanol of formula IV is present in the reaction mixture in an amount of about 0.01 mole percent based upon the moles of the compound of formula I up to an amount in which it takes on the function of the solvent. An addition of 1-85 mole percent, especially 5-65 mole percent of silanol is preferred. The mole percent of silanol is based on the moles of the compound of formula I.

The present catalytic isomerization, can, if desired, be carried out in an inert solvent and in the presence of, or with the exclusion of air. As the solvent, any conventional inert organic solvent can be utilized. Suitable solvents are, for example, aliphatic hydrocarbons such as, for example, heptane, cyclohexane, cyclodedecane, decalin, paraffin and paraffin oil, aromatic hydrocarbons such as, for example, benzene, nitrobenzene, toluene and xylene, halogenated hydrocarbons such as, for example, chlorobenzene, ethers such as, for example, anisole or dioxane or amines. Polymeric silicon-containing solvents such as silicon oils containing aliphatic or aromatic groups (e.g., methyl phenyl polysiloxane) can be used. As mentioned earlier, a silanol of formula IV can be added to the mixture in an excess amount and can thus also serve as a solvent. Therefore, excess silanol of formula IV can be utilized in the solvent in carrying out this reaction.

In carrying out this rearrangement reaction, temperature and pressure are not critical, and this reaction can be suitably carried out at a temperature of between about room temperature (20° C.) and the boiling point of the reaction mixture and at atmospheric pressure. Preferably, the reaction is carried out at a temperature of from 40° C. to 110° C. However, temperatures greater than 110° C. such as 200° C. can be utilized. However, since the reaction of this invention can be carried out at low temperatures, no beneficial results are achieved from utilizing high temperatures such as greater than 200° C. Therefore, it is not necessary to utilize such high temperatures. If desired, the isomerization can also be carried out under pressure, in which case pressures of from 1 atmosphere to about 50 atmospheres can be used. Isomerization can take place immediately upon reaction. As far as yields are concerned, the preferred isomerization time can vary within wide ranges. In general, it amounts to about 2–20 hours. If desired, reaction times of 120 hours or longer can be utilized without deleteriously affecting this reaction. However, since there is no additional beneficial results from prolonged heating, the use of long reaction times only adds additional expense to carrying out the reaction. The catalyst system containing siloxy vanadium oxide catalyst and silanol employed in the present isomerization retains practically its complete activity during the isomerization. It can therefore be used again for carrying out many (ca 100–200) isomerization batches.

The isomerization product is separated from the unreacted portions of the carbinol starting material in the usual manner; for example, by rectification. The unreacted carbinol portions can again be employed in the next batch. With this procedure there are obtained, in general, conversions of 70% to 99.9%, and, depending on the carbinol starting material employed, yields of more than 90%.

The following Examples are illustrative but not limitative of the present invention. The term "dehydrolinalool" designates 3,7-dimethyl-3-hydroxy-oct-6-en-1-yne. The term "citral" designates 3,7-dimethyl-octa-2,6-dien-1-al.

EXAMPLE 1

15.2 g. of dehydrolinalool, 1.1 g. of tris-(triphenyl-siloxy)-vanadium oxide, 6.5 g. of tri-(p-fluorophenyl)-silanol and 100.0 ml. of high-boiling paraffin oil [$D_{20}^4 =$ 0.885] are heated to 115° C. in a nitrogen atmosphere for about 4 hours. The mixture is subsequently cooled to 70° C. and, at this temperature, subjected firstly to a simple distillation and thereafter to a vacuum distillation [0.1 mm Hg]. In the last 30 minutes of the distillation the temperature is increased to 140° C. so that all liquid components distill over. The residual catalyst-/paraffin oil mixture can again be employed, as mentioned earlier, for the isomerization of further 15.2 g. batches of dehydrolinalool. The average results of 10 isomerizations carried out with the same catalyst are as follows:
-conversion of dehydrolinalool = 93.0%
-yield of citral = 96.0%

EXAMPLE 2

15.2 g. of dehydrolinalool, 1.4 g. of tris-(triphenyl-siloxy)-vanadium oxide, 4.8 g. of tri-(p-chlorophenyl)-silanol and 180 ml. of high-boiling paraffin oil [$D_{20}^4 =$ 0.885] are heated to 115° C. for 5 hours with stirring. The reaction is carried out in the same manner as Example 1. The yield of citral based on reacted dehydrolinalool amounts to 93% and the degree of conversion to ca 90%.

The same catalyst can be used for many further isomerizations.

EXAMPLE 3

15.2 g. of dehydrolinalool, 2.1 g. of tris-(triphenyl-siloxy)-vanadium oxide, 4.5 g. of tri-(p-bromophenyl)-silanol and 200 ml. of high-boiling paraffin oil [$D_{20}^4 =$ 0.885] are heated to 120° C. for 4.5 hours and reacted in the same manner as in Example 1. The yield of citral based on reacted dehydrolinalool amounts to 88.0%.

EXAMPLE 4

462 ml. of paraffin oil [$D_{20}^4 = 0.855$], 185 g. of triphenyl silanol and 31.3 g. of dehydrolinalool are mixed together with stirring and heated to 110° C. in an atmosphere of air or in an inert gas atmosphere. The clear, light-yellow colored solution which results after the addition of 5.6 g. of tris[tri-$\alpha$, $\alpha$, $\alpha$-trifluoro-m-tolyl)-siloxy]-vanadium oxide is stirred at 105°–110° C. for 6 hours. The mixture is thereafter cooled to about 80° C. and distilled under reduced pressure [0.1–0.5 mm Hg.]. The citral which passes over at 50°–60° C,> 1 mm Hg., is distilled off completely. The temperature is thereby raised to about 140° C. for about 15 minutes towards the end of the distillation.

After the removal of the citral, a new isomerization batch can be processed immediately by treating the residual parrafin oil/catalyst mixture at 110° C. with 31.3 g. of dehydrolinalool as described above. The average results obtained of 50 isomerizations carried with the same catalyst are as follows:
-overall yield of citral = 88.6%

EXAMPLE 5

0.5 g. of tri-($\alpha$, $\alpha$, $\alpha$-trilfluoro-m-tolyl)-silanol [m.p.: 72°–73° C.] are dissolved in 30 ml. of absolute benzene. The solution is treated with 0.115 g. of tris-(trimethyl siloxy)-vanadium oxide. The mixture is stirred for 1 hour at the boiling point. In a first step thereafter, 20 ml. of benzene, together with the resulting trimethyl silanol, are distilled off under atmospheric pressure and, in a second step, after the addition of 20 ml. of toluene, 20 ml. of a mixture of benzene and toluene are distilled off at atmospheric pressure. The remaining toluene solution is distilled off under reduced pressure at 50° C. The resulting tris-[tri-($\alpha$, $\alpha$, $\alpha$-trifluoro-m- tolyl)-siloxy]-vanadium oxide shows a mol peak at 1504.

EXAMPLE 6

By the procedure of Example 5:

tris-(trimethyl siloxy)-vanadium oxide is reacted with tris-(α, α, α-trifluoro-p-tolyl)-silanol to produce the tris-[tri-(α, α, α-trifluoro-p-tolyl)-siloxy]-vanadium oxide [mol peak [= 1504];

tris-(trimethyl siloxy)-vanadium oxide is reacted with tris-(p-fluorophenyl)-silanol and triphenyl-silanol in a mol ratio of 1:1:2 parts by volume to produce (tri-p-fluorophenyl)-siloxy-bis-(triphenyl-siloxy)-vanadium oxide [m.p.: 203° C.];

tris-(trimethyl siloxy)-vanadium oxide is reacted with tri-(p-fluorophenyl)-silanol and triphenyl-silanol in a mol ratio of 1:2:1 parts to volume to produce bis-[tri-(p-fluorophenyl)-siloxy]-triphenyl siloxy vanadium oxide [mol peak = 1000];

tris-(trimethyl siloxy)-vanadium oxide is reacted with tri-(p-bromophenyl)-silanol and cyclohexanol in a mol ratio of 1:2:1 parts by volume to produce bis-[tri-(p-bromophenyl)-siloxy]-cyclohexyloxy-vanadium oxide [mol peak = 1184 ref. to$^{79}$Br]; and tris-(trimethyl siloxy)-vanadium oxide is reacted with bis-(3-nitro-4-bromophenyl)-(4-bromophenyl)-silanol to produce tris-[bis-(3-nitro-4-bromophenyl)-(4-bromophenyl)-siloxy]-vanadium oxide [mol peak = 600 ref. to$^{79}$Br].

EXAMPLE 7

10 g. of 3-methyl-but-1-yn-3-ol and 8.0 g. of triphenyl-silanol are heated to 105° C. for 12 hours in 462 ml. of paraffin oil [$D_{20}^4 = 0.885$] and the mixture is treated at this temperature with 7.5 g. of tris-[bis-(3-nitro-4-bromophenyl)-(4-bromophenyl)-siloxy]-vanadium oxide. The mixture is cooled to about 78° C. and distilled under reduced pressure, the pressure being lowered to 5 mm Hg towards the end of the distillation. The prenal [3-methyl-but-2-en-1-al] which is formed boils at 132°–133° C/730 mm Hg.

The residual mixture, consisting of the paraffin oil employed and the tris-bis(3-nitro-4-bromophenyl)-4-bromophenyl-siloxy]-vanadium oxide and triphenyl-silanol, can again be employed for the isomerization of further 10 g. batches of 3-methyl-but-1-yn-3-ol. The average results of 20 isomerizations carried out with the same catalyst are as follows:
- overall yield of prenal = 93.4%

EXAMPLE 8

By the procedure of Example 3 and utilizing the catalyst and silanol of Example 3:

3-methyl-pent-1-yn-3-ol is converted to 3-methyl-pent-2-en-1-al b.p.: 60° C/35 mm Hg.; yield = 85%;

3,6,7-trimethyl-oct-6-en-1-yn-3-ol is converted to 3,6,7-trimethyloct-2,6-dien-1-al; b.p.: 69° C./0.3 mm Hg.; yield = 91.1%;

3,7-dimethyl-4-ethyl-oct-6-en-1-yn-3-ol is converted to 3,7-dimethyl-4-ethyl-oct-2,6-dien-1-al; b.p.: 72° C/0.4 mm Hg.; yield = 78.6%;

3-[(4 or 3)-methyl-cyclohex-3-en-1-yl]-but-1-yn-3-ol is converted to 3-[(4 or 3)-methyl-cyclohex-3-en-1-yl]-but-2-en-1-al; b.p.: 60° C./0.3 mm Hg.; yield = 88.5%;

3,7-dimethyl-7-methoxy-oct-1-yn-3-ol is converted to 3,7-dimethyl-7-methoxy-oct-2-en-1-al, b.p.: 66° C/0.1 mm Hg; yield = 84.2%;

2,6-dimethyl-oct-7-yn-2,6-diol [7-hydroxydehydrolinalool] is converted to 3,7-dimethyl-oct-2-en-7-ol-1-al [7-hydroxycitral], b.p.: 98° C/0.3 mm Hg.; yield = 64.7%;

1-ethynyl-cyclohexanol is converted to a) cyclohexylidine-acetaldehyde b.p.: 48° C./1.3 mm Hg.; yield = 46.5%; and b) cyclohex-1-en-1-yl-acetaldehyde. b.p.: 48° C/1.3 mm Hg.; yield = 14.0%;

1-ethynyl-2,6,6-trimethyl-cyclohexanol is converted to a) 2,2,6-trimethyl-cyclohexylidene-acetaldehyde, b.p.: 59° C/0.6 mm Hg; yield 12.5%; and b) 2,2,6-trimethyl-cyclohex-1-en-1-yl-acetaldehyde; b.p. 50° C/0.1 mm Hg.; yield = 74.5%;

1-ethynyl-cyclopentanol is converted to cyclopentylidene-acetaldehyde; b.p.: 30° C/0.1 mm Hg; yield = 34.7%;

non-1-yn-3-ol is converted to non-2-en-1-al, b.p. 34° C/0.25 mm Hg.; yield = 38.0%;

2,5-dimethyl-hex-3-yn-2,5-diol is converted to 2,5-dimethyl-hex-2-en-5-ol-4-one; b.p. 35° C/0.2 mm Hg.; yield = 79.2%;

3,7,11-trimethyl-dodeca-6,10-dien-1-yl-3-ol [dehydronerolidol] is converted to 3,7,11-trimethyl-dodeca-2,6,10-trien-1-al [farnesal], b.p.: 86° C/0.2 mm Hg; yield = 91.6%;

3,7,11,15-tetramethyl-hexadeca-6,10,14-trien-1-yn-3-ol [dehydrogeranyllinalol] is converted to 3,7,11,15-tetramethyl-hexadeca-2,6,10,14-tetraen-1-al [geranyl-citral]; b.p. 135° C./0.2 mm Hg.; yield = 71.5%;

3,7,11,15-tetramethyl-hexadec-1-yn-3-ol [dehydroisophytol] is converted to 3,7,11,15-tetramethyl-hexadec-2-en-1-al [phytal]; b.p.: 150° C./0.3 mm Hg.; yield = 75.8%.

EXAMPLE 9

A mixture of 15.2 g. of 3-hydroxy-3,7-dimethyl-octa-6-en-1-yne [dehydrolinalool], 0.85 g. of tris-[tri-(p-bromophenyl)-siloxy]-vanadium oxide, 5.5 g. of triphenyl silanol and 200 g. of liquid paraffin (b.p.< 170° C./0.1 mm Hg.) are heated to 100° C. under an inert gas atmosphere for 15 hours. The citral formed is separated from the unreacted dehydrolinalool by rectification. The yield of citral based on reacted dehydrolinalool amounts to 94.5%.

The same catalyst can be employed in over 40 isomerization cycles for the conversion of dehydrolinalool into citral in similar high yields.

EXAMPLE 10

15.2 g. of dehydrolinalool, 0.8 g. of tris-[tri-(p-chlorophenyl)siloxy]-vanadium oxide and 2.2 g. of tricyclohexyl silanol are heated to 120° C. for 5 hours in 300 ml. of silicon oil and reacted in the manner of Example 9. The yield of citral based on reacted dehydrolinalool amounts to 92.5%.

After distilling off the liquid constituents, the isomerization to citral can be repeated numerous times after renewed addition of dehydrolinalool batches.

EXAMPLE 11

15.2 g. of dehydrolinalool, 1.4 g. of tris-[tri-α, α, α-trifluoro-p-tolyl-siloxy]-vanadium oxide, 4.8 g. of tri-(p-tolyl)-silanol and 180 ml. of high-boiling paraffin oil [$D_{20}^4 = 0.885$] are heated to 115° C. for 5 hours with stirring and reacted in the manner of Example 9. The yield of citral based on reacted dehydrolinalool amounts to 94.2%.

17

The same catalyst can be used for many further isomerizations.

EXAMPLE 12

15.2 g. of dehydrolinalool, 2.1. g. of tris-[tri-(4-biphenylyl)-siloxy]-vanadium oxide, 4.5 g. of tri-(m-tolyl)-silanol and 200 ml. of high-boiling paraffin oil [$D_{20}^4 = 0.885$] are heated to 120° C. for 4.5 hours and reacted in the manner of Example 9. The yield of citral based on reacted dehydrolinalool amounts to 86.0%.

EXAMPLE 13

15.2 g. of dehydrolinalool, 2.4 g. of tri-(p-fluorophenyl)-siloxybis-(triphenyl-siloxy)-vanadium oxide, 1.8 g. of dicyclohexyl methyl silanol and 90 ml. of high-boiling paraffin oil [$D_{20}^4 = 0.885$] are heated to 120° C. for 6 hours with the exclusion of moisture. The reaction is then carried out in the manner of Example 9. The yield of citral based on reacted dehydrolinalool amounts to 86.4%.

EXAMPLE 14

13.2 g. of 3-hydroxy-3-phenyl-prop-1-yne, 3.2 g. bis-[tri-(p-fluorophenyl)-siloxy]-[triphenyl-siloxy]-vanadium oxide, 4.15 g. of triphenyl silanol and 100 ml. of silicon oil are heated to 115° C. for 8 hours with the exclusion of moisture. The reaction is carried out in the manner of Example 9. The overall yield of cinnamaldehyde amounts to 87.6%.

EXAMPLE 15

1.04 g. of 3-methoxy-19-nor-pregn-1,3,5(10)-trien-20-yn-17-ol [mestranol], 0.12 g. of bis-[tri-(p-bromophenyl)-siloxy]-cyclohexyloxyvanadium oxide, 414 mg. of triphenyl-silanol and 20 ml. of xylene are heated for 6 hours at 120° C. The solution is cooled, diluted with hexane, filtered and concentrated to give 0.892 g. of crude product. Dissolution of the crude oil in hexane and cooling deposits 0.746 g. of yellow crystals of melting point 140°–150° C. Recrystallization from isopropanol gives 0.495 g. of 3-methoxy-19-nor-pregn-1,3,5(10),17(20)-tetraen-21-al light yellow crystals of melting point 141°–155° C.

EXAMPLE 16

15.2 g. of dehyrolinalool, 1.2 g of tris-[tri-(p-fluorophenyl)-siloxy]-vanadium oxide, 6.5 g. of tri-(p-fluorophenyl)-silanol and 100.0 ml. of highboiling paraffin oil [$D_{20}^4 = 0.885$] are heated to 115° C. in a nitrogen atmosphere for about 4 hours. The mixture is subsequently cooled to 70° C. and, at this temperature, subjected firstly to a simple distillation and thereafter to a vacuum distillation [0.1 mm Hg.]. In the last 30 minutes of the distillation, the temperature is increased to 140° C. so that all liquid components distil over. The residual catalyst/paraffin oil mixture can again be employed, as mentioned earlier, for the isomerization of further 15.2 g. batches of dehydrolinalool. The average results of 10 isomerizations carried out with the same catalyst are as follows:
- conversion of dehydrolinalool = 93%
- yield of citral = 96%

EXAMPLE 17

1 g. of tri-(p-fluorophenyl)-silanol are dissolved in 30 ml. of absolute benzene. The solution is treated, while excluding moisture, with 0.255 g. of pyridine and 0.173 g. of vanadium oxytrichloride. The mixture is stirred first for 8 hours at room temperature and then for 2 hours at the boiling point and thereafter cooled to 10° C. The precipitated pyridine hydrochloride is filtered off. The filtrate is concentrated under reduced pressure. The resulting tris-[tri-(p-fluorophenyl)-siloxy]-vanadium oxide melts at 147° C. after recrystallization from n-heptane.

EXAMPLE 18

By the procedure of Example 17:

vanadium oxytrichloride is reacted with tri-(p-chlorophenyl)-silanol [m.p.: 127°–128° C.] to produce tris-[tri-(p-chlorophenyl)-siloxy]-vanadium oxide [m.p.: 181° C.];

vanadium oxytrichloride is reacted with tri-(p-bromophenyl)-silanol [m.p.: 120°–121° C.] to produce tris-[tri-(p-bromophenyl)-siloxy]-vanadium oxide [m.p.: 175° C];

vanadium oxytrichloride is reacted with tri-4-biphenylyl-silanol [m.p.: 199°–200° C.] to produce tris-[tri-(4-biphenylyl)-siloxy]-vanadium oxide.

We claim:
1. A process for obtaining alpha, beta-unsaturated carbonyl compounds of the formula:

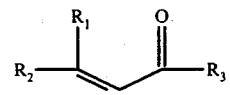

wherein $R_1$ is hydrogen or lower alkyl, $R_2$ is alkyl, alkenyl, cycloalkyl-substituted alkenyl, cycloalkyl substituted alkyl, phenyl-alkyl, phenyl-alkenyl, phenyl, cycloalkyl, cycloalkenyl, cycloalkenyl-substituted alkyl, and cycloalkenyl substituted alkenyl; $R_1$ and $R_2$ taken together with their attached carbon atom form a cycloalkyl or cycloalkenyl group, or cycloalkyl or cycloalkenyl condensed with one or more saturated or unsaturated cycloalkyl groups; $R_3$ is hydrogen, alkyl, alkenyl, phenyl alkyl, phenyl alkenyl, cycloalkyl substituted alkenyl, cycloalkyl substituted alkyl, cycloalkenyl-substituted alkyl, cycloalkenyl substituted alkenyl, phenyl, cycloalkyl or cycloalkenyl and wherein said alkyl, alkenyl, cycloalkyl, cycloalkenyl and phenyl groups are unsubstituted or substituted in one or more positions with lower alkyl, lower alkoxy, hydroxy, lower alkanoyl, aroyl, lower alkanoyloxy or aroyloxy; and wherein said alkyl, alkenyl, cycloalkyl and cycloalkenyl groups can also be substituted in one or more positions with an additional substituent selected from the group consisting of oxo or ketalized-oxo; comprising rearranging an acetylenic carbinol of the formula:

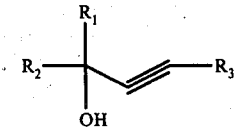

wherein $R_1$, $R_2$ and $R_3$ are as above; in the presence of a catalyst of the formula:

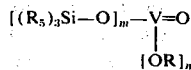

wherein $R_5$ is a hydrocarbon selected from the group consisting of lower alkyl, cycloalkyl, phenyl, phenyl (lower alkyl), phenyl substituted in one or more positions with an electron withdrawing group and phenyl lower alkyl wherein the phenyl substituent is substituted in one or more positions with an electron withdrawing group; R is $R_5$ or $-Si-(R_5)_3$; m is an integer of from 1 to 3; and n is an integer of from 0 to 1 with the proviso that the sum of m and n is 3;
and a silanol of the formula:

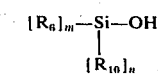

wherein m and n are as above; $R_6$ and $R_{10}$ are lower alkyl, cycloalkyl, phenyl or phenyl-lower alkyl, phenyl substituted in one or more positions with an electron withdrawing group or phenyl-lower alkyl where the phenyl substituent is substituted in one or more positions with an electron withdrawing group;
with the proviso that one of $R_5$, $R_6$ or $R_{10}$ is a phenyl or phenyl-lower alkyl group with the phenyl moiety substituted in one or more positions with an electron withdrawing group, with said electron withdrawing group being selected from the group consisting of $-NO_2$, $-C_2N$, $$-\overset{O}{\underset{\|}{C}}-CH_3, -CHO, -\overset{O}{\underset{\|}{C}}-OC_2H_5,$$

—COOH, iodine, chlorine, $-CF_3$, $-C_6H_5$, fluorine and bromine.

2. The process of claim 1, wherein the catalyst has the formula:

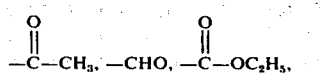

wherein $m$ and $n$ are as above; $R_5'$ is a hydrocarbon group selected from lower alkyl, cycloalkyl, phenyl or phenyl(lower alkyl) and R' is $R_5'$ or a $-Si(R_5')_3$;
and the silanol has the formula:

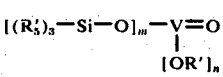

wherein $m$ and $n$ are as above; $R_5''$ is phenyl substituted in one or more positions by an electron-withdrawing group and R'' is $R_5'$ or $R_5''$.

3. The process of claim 1, wherein the catalyst has the formula:

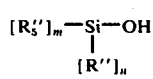

wherein $m$ and $n$ are as above; $R_5''$ is phenyl substituted in one or more positions by an electron-withdrawing group and R'' is $R_5'$ or $R_5''$; and $R_5'$ is a hydrocarbon group selected from lower alkyl, cycloalkyl, phenyl or phenyl lower alkyl;
and the silanol has the formula:

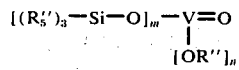

wherein $m$ and $n$ are as above; $R_5'$ is a hydrocarbon group selected from lower alkyl, cycloalkyl, phenyl or phenyl(lower alkyl).

4. The process of claim 1 wherein the catalyst has the formula:

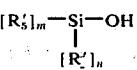

wherein $m$ and $n$ are as above; $R_5''$ is a phenyl group substituted in one or more positions with an electron withdrawing substituent and R'' is $R_5'$ and $R_5''$ and $R_5'$ is a hydrocarbon selected from the group consisting of lower alkyl, cycloalkyl, phenyl or phenyl lower alkyl;
and the silanol has the formula:

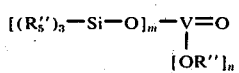

wherein $m$, $n$, R'' and $R_5''$ are as above.

5. The process of claim 2, wherein said catalyst is tris-(triphenyl-siloxy)-vanadium oxide and said silanol is tri-(p-fluoro[or p-chloro or p-bromo] phenyl-silanol.

6. The process of claim 3, wherein said catalyst is tris-[tri-(p-fluoro[or p-chloro or p-bromo]phenyl)-siloxy]-vanadium oxide and said silanol is triphenyl-silanol.

7. A process according to claim 4, wherein said catalyst is tris-[tri-(p-fluoro[or p-chloro or p-bromo]-phenyl)-siloxy]-vanadium oxide and said silanol is tri-(p-fluoro[or p-chloro or p-bromo]phenyl)-silanol.

8. The process of claim 1 wherein the rearrangement is carried out in an inert organic solvent.

9. A process according to claim 8 wherein said solvent is an aliphatic hydrocarbon.

10. A process according to claim 8, wherein said solvent is methylphenyl-polysiloxane.

11. The process according to any one of claim 1 wherein the rearrangement is carried out at a temperature of from 20° C. to the boiling point of the reaction mixture.

12. A process of claim 1 wherein said carbinol has the formula:

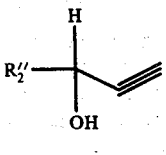

wherein R''₂ is cycloalkyl, cycloalkenyl or phenyl which may be unsubstituted or substituted by lower alkyl, lower alkoxy, hydroxy or except in the case of phenyl, by oxo or ketalized oxo;
is employed as the starting material.

13. The process of claim 12 wherein said carbinol is 3-hydroxy-3-phenyl-prop-1-yne.

14. The process of claim 1 wherein said carbinol has the formula:

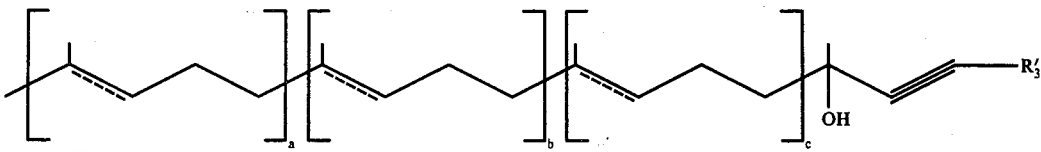

wherein R'₃ is hydrogen atom or lower alkyl and $a=1$, $b=1$ and $c=1$ or $a=0$, $b=1$ and $c=1$ or $a=0$, $b=0$ and $c=1$ or $a=0$, $b=0$ and $c=0$ and the broken lines can be hydrogenated or can contain carbon to carbon bonds and wherein hydroxy, lower alkoxy or both hydroxy and lower alkoxy substituents may be substituted on the carbon atoms in the groupings $a$, $b$ and/or $c$;
is employed as the starting material.

15. The process of claim 14 wherein said carbinol is 3-hydroxy-3-methyl-but-1-yne.

16. The process of claim 14 wherein said carbinol is 3-hydroxy-3,7-dimethyl-octa-6-en-1-yne.

17. The process of claim 14 wherein said carbinol is 3-hydroxy-3,7,11-trimethyl-dodeca-6,10-dien-1-yne.

18. The process of claim 14 wherein said carbinol is 3-hydroxy-3,7,11,15-tetramethyl-hexadeca-6,10,14-trien-1-yne.

19. The process of claim 1 wherein carbinol is 3-methoxy-19-nor-pregn-1,3,5(10)-trien-20-yn-17-ol.

20. A catalyst system consisting essentially of a mixture of a vanadate catalyst of the formula:

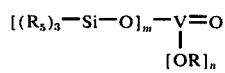

wherein R₅ is a hydrocarbon selected from the group consisting of lower alkyl, cycloalkyl, phenyl, phenyl (lower alkyl), phenyl substituted in one or more positions with an electron withdrawing group and phenyl-lower alkyl wherein the phenyl substituent is substituted in one or more positions with an electron withdrawing group; R is R₅ or —Si-(R₅)₃; $m$ is an integer of from 1 to 3; and $n$ is an integer of from 0 to 1 with the proviso that the sum of $m$ and $n$ is 3;
and at least 0.05 mole percent, based upon the moles of said vanadate catalyst of a silanol of the formula:

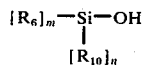

wherein $m$ and $n$ are as above; R₆ and R₁₀ are lower alkyl, cycloalkyl, phenyl or phenyl-lower alkyl, phenyl substituted in one or more positions with an electron withdrawing group or phenyl-lower alkyl where the phenyl substituent is substituted in one or more positions with an electron withdrawing group;
with the proviso that one of R₅, R₆ or R₁₀ is a phenyl or phenyl-lower alkyl group with the phenyl moiety substituted in one or more positions with an electron withdrawing group, with said electron withdrawing group being selected from the group consisting of —NO₂, —C≡N,

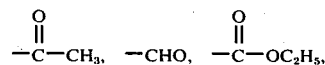

—COOH, iodine, chlorine, —CF₃, —C₆H₅, fluorine and bromine.

21. The composition of claim 20 wherein the catalyst has the formula:

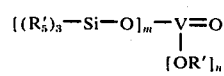

wherein $m$ and $n$ are as above; R₅' is a hydrocarbon group selected from lower alkyl, cycloalkyl, phenyl and phenyl (lower alkyl) and R' is R₅' or a -Si (R₅')₃;
and the silanol has the formula:

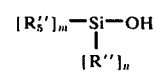

wherein $m$ and $n$ are as above; R₅'' is phenyl substituted in one or more positions by an electron-withdrawing group and R'' is R₅' or R₅''.

22. The compositions of claim 20 wherein the catalyst has the formula:

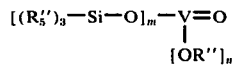

wherein $m$ and $n$ are as above; R₅'' is phenyl substituted in one or more positions by an electron-withdrawing group and R'' is R₅' or R₅''; and R₅' is a hydrocarbon group selected from lower alkyl, cycloalkyl, phenyl or phenyl lower alkyl;
and the silanol has the formula:

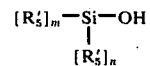

wherein $m$ and $n$ are as above; R₅' is a hydrocarbon group selected from lower alkyl, cycloalkyl, phenyl or phenyl(lower alkyl).

23. The composition of claim 20 wherein said catalyst has the formula:

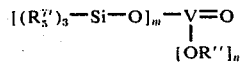

wherein $m$ and $n$ are as above; $R_5''$ is a phenyl group substituted in one or more positions with an electron withdrawing group and $R''$ is $R_5'$ or $R_5''$; and the silanol has the formula:

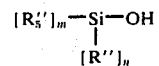

wherein $m$, $n$, $R''$ and $R_5''$ are as above.

24. The composition of claim 21 wherein said catalyst is tris-(triphenyl-siloxy)-vanadium oxide and said silanol is tri-(p-fluoro[or p-chloro or p-bromo] phenyl-silanol.

25. The composition of claim 22 wherein said catalyst is tris-[tri-(p-fluoro[or p-chloro or p-bromo]-phenyl)-siloxy]-vanadium oxide and said silanol is triphenyl-silanol.

26. The composition of claim 23 wherein said catalyst is tris-[tri-(p-fluoro[or p-chloro or p-bromo]-phenyl)-siloxy]-vanadium oxide and said silanol is tri-(p-fluoro[or p-chloro or p-bromo]phenyl)-silanol.

* * * * *